United States Patent
Ren et al.

(10) Patent No.: US 6,488,837 B1
(45) Date of Patent: Dec. 3, 2002

(54) METHANOL SENSOR OPERATED IN A PASSIVE MODE

(75) Inventors: Xiaoming Ren, Los Alamos, NM (US); Shimshon Gottesfeld, Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 65 days.

(21) Appl. No.: 09/730,142

(22) Filed: Dec. 4, 2000

(51) Int. Cl.[7] ............... G01N 27/406; H01M 10/48
(52) U.S. Cl. ............... 205/787; 204/421; 204/422; 429/90
(58) Field of Search .................. 204/421–429, 204/415, 431, 432; 205/782.5, 783.5, 787

(56) References Cited

U.S. PATENT DOCUMENTS 3,852,169 A * 12/1974 Kring et al.
5,302,274 A * 4/1994 Tomantschger et al.
5,573,866 A 11/1996 Van Dine et al. ............. 429/13

OTHER PUBLICATIONS

Barton et al., "A Methanol Sensor for Portable Direct Methanol Fuel Cells, " J. Electrochem. Soc., vol. 145, No. 11, pp. 3783–3788, Nov. 1998.

* cited by examiner

Primary Examiner—T. Tung
(74) Attorney, Agent, or Firm—Ray G. Wilson

(57) ABSTRACT

A sensor outputs a signal related to a concentration of methanol in an aqueous solution adjacent the sensor. A membrane electrode assembly (MEA) is included with an anode side and a cathode side. An anode current collector supports the anode side of the MEA and has a flow channel therethrough for flowing a stream of the aqueous solution and forms a physical barrier to control access of the methanol to the anode side of the MEA. A cathode current collector supports the cathode side of the MEA and is configured for air access to the cathode side of the MEA. A current sensor is connected to measure the current in a short circuit across the sensor electrodes to provide an output signal functionally related to the concentration of methanol in the aqueous solution.

3 Claims, 2 Drawing Sheets

METHANOL SENSOR OPERATED IN A PASSIVE MODE

STATEMENT REGARDING FEDERAL RIGHTS

This invention was made with government support under Contract No. W-405-ENG-36 awarded by the U.S. Department of Energy. The government has certain rights in the invention.

BACKGROUND OF THE INVENTION

A methanol sensor is an important component in a direct methanol fuel cell power system. The sensor is used to monitor the concentration of methanol solution fed to the fuel cell anode electrode. Based on the response of the sensor, active control of the methanol concentration to the desired level can be achieved.

Barton et al., "A Methanol Sensor for Portable Direct Methanol Fuel Cell,"145 *J. Electrochem. Soc.*, pp. 3783–3788 (1998), report the design of such methanol sensor, based on studies (X. Ren et al., 1 *Proton Conducting Membrane Fuel Cells*, Ed. Gottesfeld et al., pg. 284 (The Electrochemical Society, Pennington, N.J. (1995)) of methanol transportation across a polymer electrolyte membrane such as that used in a direct methanol fuel cell. The two sensor electrodes were prepared similarly as fuel cell electrodes by applying catalyst, usually Pt containing catalyst powder, and recast ionomer mixture to the polymer electrolyte membrane to form membrane electrode assembly (MEA). The MEA is exposed to the methanol solution on one side, and the methanol flux across the membrane is electro-oxidized at the other side of the MEA by applying an external voltage across the two electrodes. With a sufficiently high electrode activity, achieved by both high catalyst layer activity and a high voltage across the two electrodes, a limiting current, which is approximately proportional to the methanol concentration for a low methanol concentration range, can be measured as the response of the sensor. $H_2$ evolution reaction occurs concomitantly on the counter electrode that is exposed to the methanol solution.

For this type of sensor, the interference of oxygen from air has to be dealt with by either limiting the air access to the methanol electro-oxidation electrode or applying a high voltage (about 1 volt.) across the sensor electrodes to limit the oxygen electro-reduction reaction. Because the sensor is operated with an external power source to drive the electrode reactions, the sensor is characterized as operating in a driven mode, with the need of consuming external electric power.

The present invention provides a self-driven sensor, i.e., no applied voltage is required, to measure the concentration of methanol in an adjacent aqueous solution. The methanol sensor is generally a direct methanol fuel cell with a membrane electrode assembly (MEA) containing a methanol electro-oxidation anode and an air ($O_2$) electro-reduction cathode. Methanol access from the aqueous solution to the anode side of the MEA is limited to diffusion through a physical barrier, which can be an aperture opening with defined geometry, a porous medium, or the like. The anode and the cathode are shorted together through an electrical connection so all the methanol that reaches the anode side is completely consumed at the anode with concomitant oxygen reduction at the cathode. All the reactions are self-driven and no external voltage source is required. The current passing through the shorting connection is limited by diffusion of methanol through the barrier so that the current is directly related to the methanol concentration in the aqueous solution.

Various advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

The present invention includes a sensor for outputting a signal related to a concentration of methanol in an aqueous solution adjacent the sensor. A membrane electrode assembly (MEA) is included with an anode side and a cathode side. An anode current collector supports the anode side of the MEA and has a flow channel therethrough for flowing a stream of the aqueous solution and forms a physical barrier to control access of the methanol to the anode side of the MEA. A cathode current collector supports the cathode side of the MEA and is configured for air access to the cathode side of the MEA. A current sensor is connected to measure the current in a short circuit across the sensor electrodes to provide an output signal functionally related to the concentration of methanol in the aqueous solution.

BRIEF DESCRIPTION OF THE DRAWINGS

The accompanying drawings, which are incorporated in and form a part of the specification, illustrate the embodiment(s) of the present invention and, together with the description, serve to explain the principles of the invention. In the drawings.

DETAILED DESCRIPTION

Figure 1:
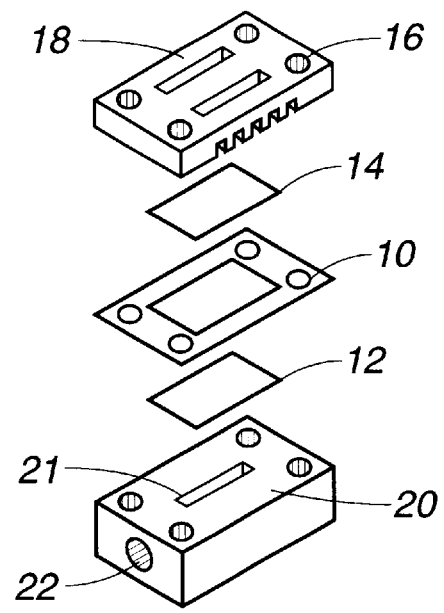
FIG. 1 is a pictorial illustration in exploded view of a methanol sensor according to an exemplary embodiment of the present invention.

In accordance with the present invention, the air cathode and methanol anode of the sensor self-drive the electrode reactions, as in a direct methanol fuel cell. This sensor differs from those sensors reported by Barton et al. in that the sensor design eliminates the need for an external power source and avoids interference of oxygen from the air with the methanol electrode.

The methanol sensor consists of the anode and cathode current collectors, which sandwich a membrane electrode assembly (MEA). There are usually an anode backing and a cathode backing between the membrane electrode assembly and the current collectors. As in a direct methanol fuel cell, the MEA has a methanol oxidation anode catalyst layer and an oxygen reduction cathode catalyst layer attached to a polymer electrolyte membrane. For the methanol electro-oxidation anode, a Pt or PtRu catalyst is usually used, while for the oxygen electro-reduction cathode, a Pt catalyst is usually used. The catalyst, in the form of carbon supported or un-supported powder with a high surface area, is first mixed with deionized water in about 1:10 weight ratio, then with a suitable amount of recast Nafion® ionomer to form an ink mixture. The anode and cathode ink mixtures are then applied to a polymer electrolyte membrane, such as a Nation® membrane, to form the MEA.

During the operation of the sensor, the anode side of the MEA exposed to a methanol solution and the cathode side to the air. By placing a physical barrier, such as a porous medium, a small hole, or a narrow slit between the bulk methanol solution and the anode, the maximum methanol flux to the anode electrode of the sensor is restricted.

The physical barrier is designed to limit the overall flux of methanol to the sensor anode to a value that is well below the rate of supply of oxygen from air to the cathode. A typical equivalent value for oxygen supply is on the order of 100 mA/cm$^2$ in an "air breathing" cathode. Therefore, the diffusion limited methanol current should be less than 10 mA/cm$^2$. A diffusion limited methanol current is determined by $$J_{D,MeOH} = \frac{6DCXF}{\delta} \leq 10 \, \text{mA/cm}^2, \quad (1)$$

where D is the diffusion coefficient of methanol (MeOH) (~10$^{-5}$ cm$^2$/cc; C is the methanol concentration, typically 0.5 M (5×10$^{-4}$ mol/cm$^3$); δ is the length of a diffusion path (e.g., the length of holes in a grid pattern); and X is the overall "open fraction" of the barrier that is open, e.g., the cross-sectional area of holes in a grid.

For example, if a barrier 1 mm thick with a grid of holes is well below the anode backing, then, from Equation (1), $$X = \frac{10^{-2} \, A/cm^2 \times 10^{-1} \, cm}{10^{-5} \, cm^2/sec \times 5 \cdot 10^{-4} \, mol/cm^3 \times 6 \cdot 10^8 \, C/mol} = \frac{1}{3}.$$

That is, one third of the area of the 1 mm thick plate should be holes.

In a suitable design, the maximum sensor current is determined by the methanol flux across the barrier. At a zero voltage across the two electrodes, i.e., a short circuit between the two electrodes, the sensor acts as an operating direct methanol fuel cell with direct access of atmospheric air to the cathode. Because the methanol flux cross the barrier is diffusion controlled, the sensor current response becomes proportional to the methanol concentration.

FIG. 1 shows a schematic diagram of an exemplary sensor implementing the present invention. The sensor comprises of a membrane electrode assembly 10, anode backing 12 and cathode backing 14, cathode current collector 16 with openings 18 to air, and anode current collector 20 with methanol flow-through flow channel 22 and a barrier 21, e.g., 0.3 in. long by 0.04 in. wide, that limits methanol diffusion to the methanol electrooxidation electrode.

Membrane electrode assembly (MEA) 10: MEA 10 was made by painting anode ink and cathode ink directly onto a proton conducting membrane, such as a polymer electrolyte membrane, a Nation® 117 membrane in particular, over a vacuum table at 60° C. The anode ink was made from PtRu catalyst (1:1 atomic ratio of Pt:Ru) and N1200 equivalent weight (EW) ionomer solution, and the cathode ink from Pt catalyst and N1200 EW ionomer solution. The dry anode and cathode inks contained 15% and 10% recast Nation® component by weight, respectively. The catalyst loadings were 8 mg PtRu/cm$^2$ on the anode and 6 mg Pt/cm$^2$ on the cathode.

Anode backing 12: A hydrophilic single sided carbon cloth backing (E-TEK 2.02) was used to contact the active area at the anode side of the MEA.

Cathode backing 14: A hydrophilic double-sided carbon cloth backing (E-TEK NC/DS/V2) was used to contact the active area at the cathode side of the MEA. Like the operation of a direct methanol fuel cell, there is a substantial water flux associated with the protonic current across the polymer electrolyte membrane from anode to cathode. The desired hydrophobicity of the cathode backing provided by the polytetrafluoroethylene (PTFE) component enhances the performance stability of the air cathode against possible flooding. Flooding problems also can be alleviated or eliminated by using an oversized cathode electrode that gives higher O$_2$ reduction activity and higher area for water evaporation.

Cathode current collector 16: The body of cathode current collector 16 was made of 316 L stainless steel. Air breathing channel and openings 18 were made through current collector 16 to enhance air access to the cathode catalyst layer and water evaporation from the cathode backing.

Anode current collector 20: The body of anode current collector 20 was made of 316 L stainless steel. For the exemplary methanol flow-through sensor, there was also a methanol flow channel 22 formed within anode current collector 26. Between the bulk methanol solution in methanol flow-through channel 26 and sensor anode backing 12, a narrow slit opening 21 was made to restrict the maximum methanol flux to anode electrode backing 12. It will be appreciated that a number of barrier designs can be used with alternate opening geometries or, alternatively, a methanol barrier, such as another Nafion® membrane, in order to restrict methanol access to MEA 10 anode side. The sensor components were assembled with four insulated screws at the corners as shown in FIG. 1.

Figure 2:
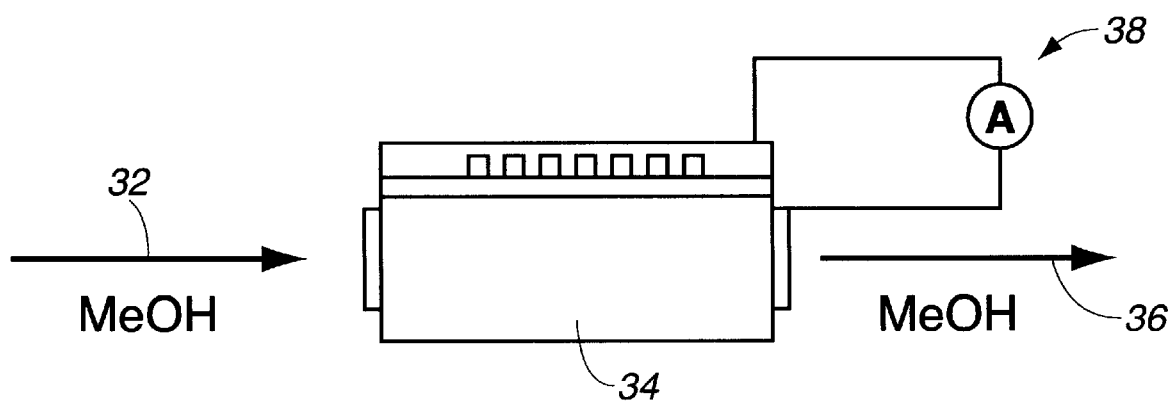
FIG. 2 is a schematic diagram of an experimental set-up for testing the response of the sensor shown in FIG. 1 to the concentration of various methanol solutions.

The experimental set-up to test the response of the sensor shown in FIG. 1 to a methanol solution is shown in FIG. 2. The temperature of methanol solution 32 was controlled by pumping methanol solution 32 through a stainless steel coil in a thermostated oven (not shown) before feeding through sensor 34. The response of sensor 34 to the concentration of the methanol solution was measured with zero impedance current sensor, such as an amperemeter or Hall effect sensor, as the current flows in the external circuit 38 from cathode to anode when the two electrodes are shorted.

Figure 3:
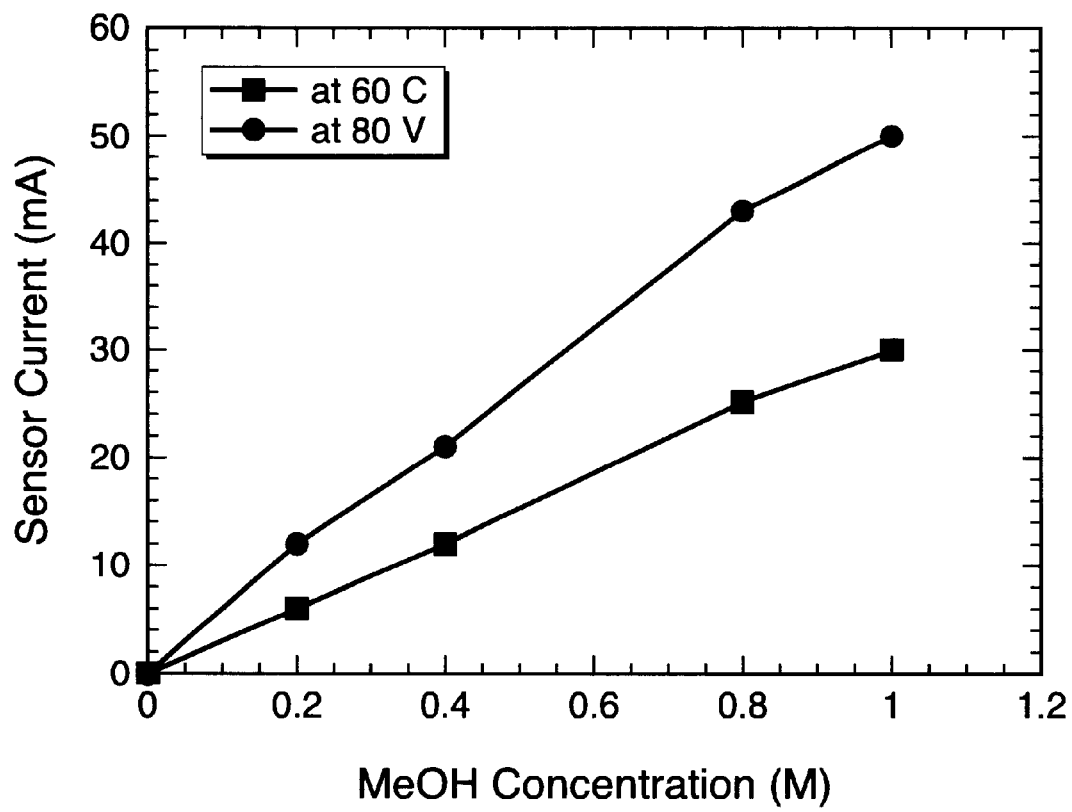
FIG. 3 graphically depicts the response of the sensor shown in FIG. 1 to different methanol concentrations at 60 and 80° C. at zero applied voltage across the anode and cathode.

FIG. 3 shows the sensor current response to various methanol solutions at 60 and 80° C. under a short circuit applied across the sensor anode and cathode. The measured current response of the sensor under the short circuit condition showed a good linear relationship with the methanol concentration over the test concentration range. The sensor response time in a change from deionized water to a methanol solution feed at 20 ml/min was 10 to 15 seconds.

The test results for the passive mode sensor described herein show that:

(a). The measured sensor current is the limiting current of methanol electro-oxidation due to the restricted methanol flux through the slit.

(b). The sensor is self-driven and showed a good linear response to the methanol concentration range used in direct methanol fuel cells.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A sensor for outputting a signal related to a concentration of methanol in an aqueous solution adjacent the sensor comprising:

a membrane electrode assembly (MEA) having an anode side for methanol oxidation and a cathode side for oxygen reduction;

an anode current collector supporting the anode side of the MEA and having a flow channel therethrough for flowing a stream of the aqueous solution and forming a physical barrier to control access of the methanol to the anode side of the MEA;

a cathode current collector supporting the cathode side of the MEA and open to the atmosphere for air access over the cathode side of the MEA; and a current sensor connected to measure current in a short circuit across the anode and cathode current collectors to provide an output signal functionally related to the concentration of methanol in the aqueous solution.

2. The sensor according to claim 1, wherein the physical barrier for the methanol provides a diffusion limited methanol flux across the barrier.

3. A method for determining the concentration of methanol in an aqueous solution comprising:

providing a membrane electrode assembly (MEA) having a cathode side and an anode side;

providing direct atmospheric air access to the cathode side of the MEA;

limiting access of the methanol to the anode side of the MEA to diffusion from the aqueous solution; and sensing an output electrical current functionally related to the concentration of methanol in the aqueous solution by a current sensor connected in a short circuit across the cathode side and the anode side of the electrode assembly.

* * * * *